(12) United States Patent
Wallace et al.

(10) Patent No.: US 7,695,484 B2
(45) Date of Patent: *Apr. 13, 2010

(54) POLYMER COVERED VASO-OCCLUSIVE DEVICES AND METHODS OF PRODUCING SUCH DEVICES

(75) Inventors: Michael P. Wallace, Pleasanton, CA (US); Dewlilah Yin Hui, Union City, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 368 days.

This patent is subject to a terminal disclaimer.

(21) Appl. No.: 11/089,829

(22) Filed: Mar. 24, 2005

(65) Prior Publication Data
US 2005/0192621 A1    Sep. 1, 2005

Related U.S. Application Data

(63) Continuation of application No. 10/139,096, filed on May 3, 2002, now abandoned, which is a continuation of application No. 09/874,181, filed on Jun. 4, 2001, now abandoned, which is a continuation of application No. 09/326,188, filed on Jun. 4, 1999, now Pat. No. 6,280,457.

(51) Int. Cl.
*A61B 17/00* (2006.01)
(52) U.S. Cl. .................................................. 606/157
(58) Field of Classification Search ............. 606/108, 606/151, 157, 127, 200, 159; 623/1.12, 1.13, 623/1.23, 1.43, 1.46
See application file for complete search history.

(56) References Cited

U.S. PATENT DOCUMENTS

| | | | |
|---|---|---|---|
| 3,174,851 A | 3/1965 | Buehler et al | |
| 3,351,463 A | 11/1967 | Rozner et al | |
| 3,753,700 A | 8/1973 | Harrison et al | |
| 4,739,768 A | 4/1988 | Engelson | |
| 4,820,298 A | 4/1989 | LeVeen et al. | |
| 4,990,158 A * | 2/1991 | Kaplan et al. | 623/1.46 |
| 4,994,069 A | 2/1991 | Ritchart et al. | |
| 5,122,136 A | 6/1992 | Guglielmi et al. | |
| 5,226,911 A | 7/1993 | Chee et al. | |
| 5,234,437 A | 8/1993 | Sepetka | |

(Continued)

FOREIGN PATENT DOCUMENTS

EP    0826342 A    3/1998

(Continued)

OTHER PUBLICATIONS

Notice of Rejection for related Japanese Patent Application No. 2001-501117, mailing date Mar. 4, 2008, including Japanese language version of Notice and associate's translation, (8 pages).

(Continued)

*Primary Examiner*—Kevin T Truong
(74) *Attorney, Agent, or Firm*—Vista IP Law Group LLP

(57) ABSTRACT

This is a medical device for forming an embolism within the vasculature of a patient. More particularly, it concerns an occlusion device comprising an inner core covered with a polymer. The medical device encourages cellular attachment and growth while maintaining favorable handling, deployment and visualization characteristics.

22 Claims, 8 Drawing Sheets

U.S. PATENT DOCUMENTS

| | | |
|---|---|---|
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford et al. |
| 5,312,415 A | 5/1994 | Palermo |
| 5,350,397 A | 9/1994 | Palermo et al. |
| 5,354,295 A | 10/1994 | Guglielmi et al. |
| 5,382,259 A | 1/1995 | Phelps et al. |
| 5,382,260 A | 1/1995 | Dormandy, Jr. et al. |
| 5,417,708 A | 5/1995 | Hall et al. |
| 5,423,829 A | 6/1995 | Pham et al. |
| 5,423,849 A | 6/1995 | Engelson et al. |
| 5,522,822 A | 6/1996 | Phelps et al. |
| 5,527,338 A | 6/1996 | Purdy |
| 5,536,274 A * | 7/1996 | Neuss ................. 623/1.22 |
| 5,549,624 A | 8/1996 | Mirigian et al. |
| 5,582,619 A | 12/1996 | Ken |
| 5,624,461 A | 4/1997 | Mariant |
| 5,639,277 A | 6/1997 | Miariant et al. |
| 5,645,082 A | 7/1997 | Sung et al. |
| 5,645,558 A | 7/1997 | Horton |
| 5,649,949 A | 7/1997 | Wallace et al. |
| 5,669,931 A | 9/1997 | Kupiecki et al. |
| 5,690,666 A | 11/1997 | Berenstein et al. |
| 5,700,258 A | 12/1997 | Mirigian et al. |
| 5,718,711 A | 2/1998 | Berenstein et al. |
| 5,749,894 A * | 5/1998 | Engelson ................. 606/213 |
| 5,792,154 A | 8/1998 | Doan et al. |
| 5,797,953 A | 8/1998 | Tekulve |
| 5,830,230 A | 11/1998 | Berryman et al. |
| 5,843,118 A | 12/1998 | Sepetka et al. |
| 5,853,418 A | 12/1998 | Ken et al. |
| 5,863,366 A | 1/1999 | Snow |
| 5,911,731 A * | 6/1999 | Pham et al. ................. 606/191 |
| 5,984,929 A * | 11/1999 | Bashiri et al. ................. 606/108 |
| 6,280,457 B1 | 8/2001 | Wallace et al. |
| 6,331,188 B1 * | 12/2001 | Lau et al. ................. 623/1.13 |

FOREIGN PATENT DOCUMENTS

| | | |
|---|---|---|
| EP | 0739608 A | 10/1998 |
| JP | 06319743 | 11/1994 |
| JP | 10024039 | 1/1998 |
| WO | 9858590 | 12/1998 |

OTHER PUBLICATIONS

Office Action for related JP patent application No. 2001-501117 mailing date Dec. 2, 2008, in Japanese language with translation provided by Japanese associate. (4 pages).

* cited by examiner

POLYMER COVERED VASO-OCCLUSIVE DEVICES AND METHODS OF PRODUCING SUCH DEVICES

This application is a continuation of application Ser. No. 10/139,096, filed May 3, 2002, which is a continuation of application Ser. No. 09/874,181, filed Jun. 4, 2001, which is a continuation of application Ser. No. 09/326,188, filed Jun. 4, 1999, now U.S. Pat. No. 6,280,457.

FIELD OF THE INVENTION

This invention relates to a medical device for forming an embolism within the vasculature of a patient. More particularly, it concerns an occlusion device comprising an inner core covered with a polymer. The device encourages cellular attachment and growth while maintaining favorable handling, deployment and visualization characteristics.

BACKGROUND

Vaso-occlusive devices are surgical implements that are placed within open sites in the vasculature of the human body. The devices are introduced typically via a catheter to the site within the vasculature that is to be closed. That site may be within the lumen of a blood vessel or perhaps within an aneurysm stemming from a blood vessel.

There are a variety of materials and devices which have been used to create such emboli. For instance, injectable fluids such as microfibrillar collagen, various polymeric foams and beads have also been used. Polymeric resins, particularly cyanoacrylate resins, have been used as injectable vaso-occlusive materials. Both the injectable gel and resin materials are typically mixed with a radio-opaque material to allow accurate siting of the resulted material. There are significant risks involved in use of a cyanoacrylates, because of the potential for misplacement. Such a misplacement would create emboli in undesired areas. Cyanoacrylate resins or glues are somewhat difficult, if not impossible, to retrieve once they are improperly placed.

Other available vaso-occlusive devices include mechanical vaso-occlusive devices. Examples of such devices are helically wound coils, ribbons and braids. Various shaped coils have been described. For example, U.S. Pat. No. 5,624,461 to Mariant describes a three-dimensional in-filling vaso-occlusive coil. U.S. Pat. No. 5,639,277 to Mariant et al. describe embolic coils having twisted helical shapes and U.S. Pat. No. 5,649,949 to Wallace et al. describes variable cross-section conical vaso-occlusive coils. A random shape is described, as well. U.S. Pat. No. 5,645,082 to Sung et al., describes methods for treating arrhythmia using coils which assume random configurations upon deployment from a catheter. U.S. Pat. No. 5,527,338 to Purdy describes a multi-element intravascular occlusion device in which shaped coils may be employed. Substantially spherical shaped occlusive devices are described in U.S. Pat. No. 5,423,829 to Pham and Doan. U.S. Pat. No. 5,690,666 entitled "Ultrasoft Embolization Coils with Fluid-Like Properties" by Berenstein et al., describes a coil having little or no shape after introduction into the vascular space.

There are a variety of ways of discharging shaped coils and linear coils into the human vasculature. In addition to those patents which suggest the physical pushing of a coil out into the vasculature (e.g., U.S. Pat. No. 4,994,069 to Ritchart et al.), there are a number of other ways to release the coil at a specifically chosen time and site. U.S. Pat. No. 5,354,295 and its parent, U.S. Pat. No. 5,122,136, both to Guglielmi et al., describe an electrolytically detachable embolic device.

A variety of mechanically detachable devices are also known. For instance, U.S. Pat. No. 5,234,437, to Sepetka, shows a method of unscrewing a helically wound coil from a pusher having interlocking surfaces. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlocking ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when expelled from the distal tip of the catheter. U.S. Pat. No. 5,312,415, to Palermo, also shows a method for discharging numerous coils from a single pusher by use of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and will then be released upon pushing the axially placed pusher wire against the member found on the proximal end of the vaso-occlusive coil.

In addition, several patents describe deployable vaso-occlusive devices that have added materials designed to increase their thrombogenicity. For example, fibered vaso-occlusive devices have been described at a variety of patents assigned to Target Therapeutics, Inc., of Fremont, Calif. Such vaso-occlusive coils having attached fibers is shown in U.S. Pat. Nos. 5,226,911 and 5,304,194, both to Chee et al. Another vaso-occlusive coil having attached fibrous materials is found in U.S. Pat. No. 5,382,259, to Phelps et al. The Phelps et al. patent describes a vaso-occlusive coil which is covered with a polymeric fibrous braid on its exterior surface.

In other attempts to increase thrombogenesis, vaso-occlusive coils have also been treated with variety of substances. For instance, U.S. Pat. No. 4,994,069, to Ritchart et al., describes a vaso-occlusive coil that assumes a linear helical configuration when stretched and a folded, convoluted configuration when relaxed. The stretched condition is used in placing the coil at the desired site (by its passage through the catheter) and the coil assumes a relaxed configuration— which is better suited to occlude the vessel—once the device is so placed. Ritchart et al. describes a variety of shapes. The secondary shapes of the disclosed coils include "flower" shapes and double vortices. The coils may be coated with agarose, collagen or sugar.

U.S. Pat. No. 5,669,931 to Kupiecki et al. discloses coils that may be filed or coated with thrombotic or medicinal material. U.S. Pat. No. 5,749,894 to Engleson discloses an aneurysm closure method which involves a reformable polymer.

U.S. Pat. No. 5,536,274 to Neuss shows a spiral implant which may assume a variety of secondary shapes. Some complex shapes can be formed by interconnecting two or more of the spiral-shaped implants. To promote blood coagulation, the implants may be coated with metal particles, silicone, PTFE, rubber lattices, or polymers.

None of the documents described above suggest a device such as that claimed herein.

SUMMARY OF THE INVENTION

This invention relates to devices and to methods for making vaso-occlusive devices typically at least partially covered by a polymeric fiber. The vaso-occlusive device often will have a primary shape of a helical coil. In particular, one variation of the inventive device is a simple wire wrapped with at least one polymeric fiber. The term polymeric fiber used throughout this invention, refers to, for example, a mono-filament, such as a single filament, or a multi-filament construction, such as a plurality of single filaments wound, braided, or otherwise joined together. The wire is then formed into a primary shape of a helical coil. The helical coil may be, for example, elongated or substantially spherical. Also, the pitch of the polymeric fiber on the wire may range from, for example, open to closed, depending upon the desired density of polymer desired. The pitch of the fiber may also be consistent or vary along the wire.

Another variation of the inventive device is a wire formed into a primary shape of a helical coil with at least one polymeric fiber that is wound or braided about the helical coil, thus covering the coil. The helical coil may be, for example, elongated or substantially spherical. Also, the pitch of the polymeric fiber on the coil may range from, for example, open to closed, depending upon the desired distal density of polymer desired. For example, a fiber with an open pitch will have spaces between each turn of the fiber, while a fiber with a closed pitch will not have spaces between each turn. The proximal pitch of the polymeric fiber may also be consistent or vary along the coil.

Another variation of the inventive device is at least one polymeric fiber braided about the device. The braid covering the device may be woven with or without openings. In the case where the braid is woven without openings, the braid may be, for example, tightly braided.

Another variation of the inventive device is a polymer covered vaso-occlusive device having a primary shape substantially of a helical coil and further having a secondary shape. This secondary shape of the polymer covered device may be selected from a variety of shapes and sizes tailored for the particular use of the inventive vaso-occlusion device. Such secondary shapes are, for example, a clover-leaf, figure-8, substantially spherical, flower-shaped, vortex, ovoid, randomly shaped. The random shape includes both randomly shaped 2-D and 3-D coils. Other shapes as required for a particular use of the invention are also within the scope of this invention.

An aspect of this inventive device is that the vaso-occlusive device may be radiopaque, e.g., a radiopaque inner core wire or the addition of a radiopaque additive added to the polymeric fiber. The device may also employ a detachable tip, e.g., mechanically detachable, electrolytically detachable, etc. Yet another variation of the invention is the use of an insulative or highly resistive member proximally of the coil. The resistive or insulating member may be any suitable material such as inorganic oxides, glues, polymeric inserts, polymeric coverings, etc. This insulative or highly resistive layer or joint appears to focus the current flow through the sacrificial electrolytic joint and thereby improves the rate at which detachment of the implant occurs.

The polymeric material of the inventive device may be, but is not limited to, protein based polymers, absorbable polymers, and non-protein based polymers, or a combination thereof. The wire may be, but is not limited to gold, rhenium, platinum, palladium, rhodium, ruthenium, stainless steel, tungsten, and alloys thereof, or any combination thereof.

The polymeric material may be a carrier for various agents, for example, drugs, medicines, growth factors, or genes.

Another variation of this invention includes coils having at least one stretch-resisting member extending through the interior of the primary shape of the coil. The stretch resistant member is fixedly attached, directly or indirectly, to the coil in at least two locations. The stretch-resisting member is preferably loose within the coil to prevent binding of the coil during passage of the coil through turns in the vasculature. A stretch-resisting member may also be used in a coil with a secondary shape.

This invention further includes the process of winding or braiding at least one polymeric fiber about a wire and shaping the covered wire into a primary shape of, for example, a helical coil. Again, the polymeric fiber includes, for example, a mono-filament, such as a single filament, or a multi-filament construction, such as a plurality of filaments wound, braided, or otherwise associated or joined together. As mentioned above, the pitch of the polymeric fiber may range, for example, from open to closed, or the pitch may vary, depending upon the desired density of polymer wanted on the final device.

Another process variation of the invention includes the steps of winding or braiding at least one polymeric fiber about a mandrel, for example, a Teflon mandrel, then applying heat to the polymeric fiber. Next, the heated polymeric fiber is removed from the mandrel and attached to the a wire having a primary shape of, for example, a helical coil.

The invention may include, for example, dipping or extruding a polymeric material upon the wire and then shaping the wire into a primary shape.

The invention may also include the step of further shaping a polymeric covered wire having a primary shape into a secondary shape. This may be performed, for example, by pulling a stylet through the primary shape of the polymeric covered wire. Examples of such secondary shapes are provided above.

This invention may also includes the step of further heating a polymeric covered wire after the polymeric covered wire is shaped into a secondary shape.

This invention further includes the process of at least partially occluding an aneurysm using the inventive vaso-occlusive device as described above. For, example, the device may be deployed into the aneurysm by using a detachable tip. As described above, the detachable tip may be, for example, an electrolytically detachable or mechanically detachable tip.

As will become apparent, preferred features and characteristics of one variation and/or aspect of the invention are applicable to any other variation and/or aspect of the invention.

BRIEF DESCRIPTION OF THE DRAWINGS

FIG. 2A illustrates a variation of a polymeric covered occlusion device having a secondary shape of that of a clover leaf.

FIG. 2B illustrates a variation of a polymeric covered occlusion device having a secondary shape of that of a twisted figure-8.

FIG. 2C illustrates a variation of a polymeric covered occlusion device having a secondary shape of that of a flower.

FIG. 2D illustrates a variation of a polymeric covered occlusion device having a substantially spherical secondary shape.

FIG. 2E illustrates a variation of a polymeric covered occlusion device having a random secondary shape.

FIG. 2F illustrates a variation of a polymeric covered occlusion device having a secondary shape of that of a vortex.

FIG. 2G illustrates a variation of a polymeric covered occlusion device having an secondary shape of that of an ovoid.

DESCRIPTION OF THE INVENTION

This invention involves vaso-occlusive devices which are at least partially wrapped with polymeric fiber and methods of producing those vaso-occlusive devices.

Figure 1A:
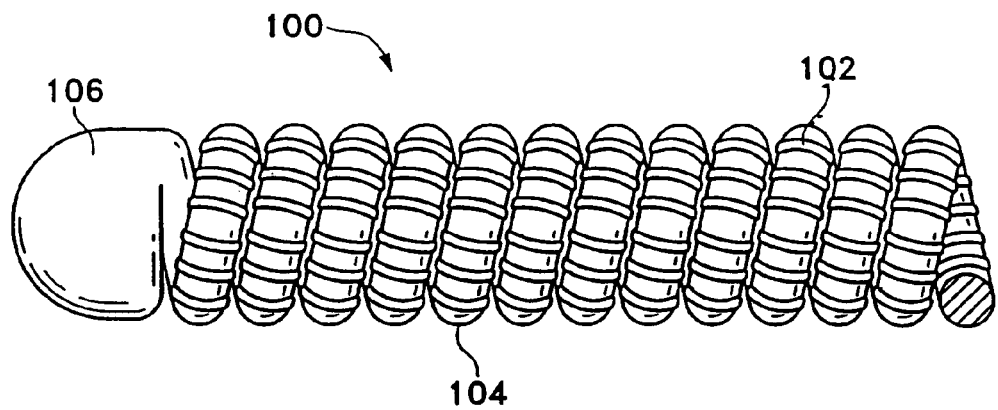
FIG. 1A shows a partial view of a polymeric covered occlusive device having a core wire having a primary shape with at least one polymeric fiber wrapped about the core wire

FIG. 1A shows a typical vaso-occlusive device (100) in which a wire (104) has been wrapped with a polymer (102) according to the procedures described herein. Vaso-occlusive device (100) is shown in FIG. 1A to comprise a primary shape of a helically wound coil (104) having tips (106) to ease the potential of the component wire to cause trauma in a blood vessel. The device is made up of a wire (104) which has been wrapped with a polymeric fiber (102). In the illustration of FIG. 1A, the fiber (102) is wrapped about the wire (104) with an open pitch. However, a closed pitch (not shown) is also contemplated. In this variation, the polymeric fiber (108) is displayed as a single filament. However, a multi-filament (not shown), such as a plurality of filaments joined together is also contemplated. The polymeric fiber (108) may be attached to the wire (110) at any (or all) points on the wire (110). Obviously, the polymeric fiber is first placed on the wire per se and the combination of fiber and wire is then made into the primary shape, i.e., the helical coil, using one of the procedures described below.

Figure 1B:
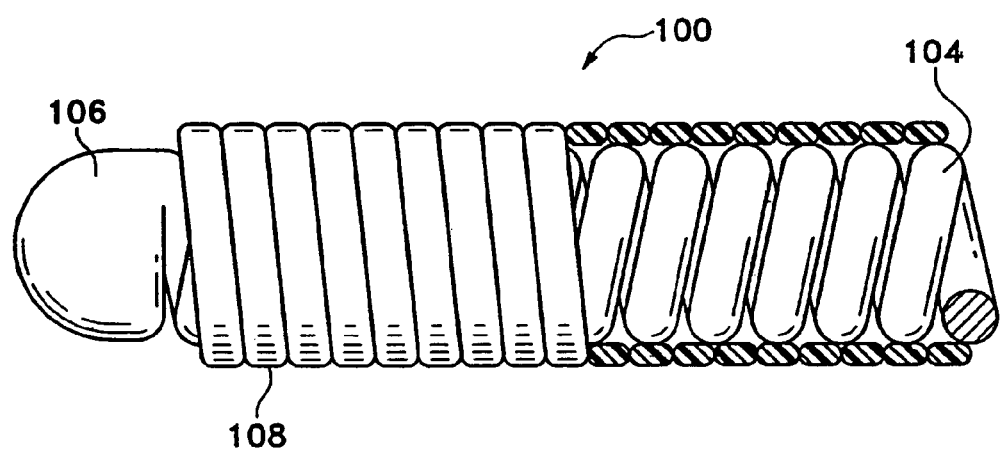
FIG. 1B shows a partial sectional view of a polymeric covered occlusive device having a core wire having a primary shape with at least one wound polymeric fiber covering the primary shape of the device.

FIG. 1B shows another variation of the vaso-occlusive device (100) in which a polymeric fiber (108) has been placed over a helically wound coil (104) which has already been formed into its primary shape. In this example, the primary shape of the device (100) is a helically wound coil. The device (100) has tips (106) to minimize the potential of the component wire to cause trauma in a blood vessel. Again, the pitch of the fiber (108) about the device (100) is shown to be closed for illustrative purposes only, it is also contemplated that the pitch may be open.

Preferably, the device (100), which may have a primary shape of a helical coil as shown in the Figures, comprises a radio-opaque, biocompatible material such as a metal or a polymer. The device (100) may be, but is not necessarily, subjected to a heating step to set the wire into the primary shape. Suitable metals may be selected from gold, rhenium, platinum, palladium, rhodium, ruthenium, various stainless steels, tungsten, and alloys thereof. The preferred alloy is one comprising upwards of 90 percent platinum and at least a portion of the remainder, tungsten. This alloy exhibits excellent biocompatibility and yet has sufficient strength and ductility to be wound into coils of primary and secondary shape and will retain those shapes upon placement of the vaso-occlusive device in the human body. The diameter of the wire typically making up the coils is often in a range of 0.005 and 0.050 inches, preferably between about 0.001 and about 0.003 inches in diameter.

The polymeric material (106, 108) covering the device may be selected from a wide variety of materials. On such example is a suture-type material which is for example, a single monofilament or multiple filaments braided or otherwise associated or joined together. Synthetic and natural polymers, such as polyurethanes (including block copolymers with soft segments containing esters, ethers and carbonates), polyethers, polyimides (including both thermosetting and thermoplastic materials), acrylates (including cyanoacrylates), epoxy adhesive materials (two part or one part epoxy-amine materials), olefins (including polymers and copolymers of ethylene, propylene butadiene, styrene, and thermoplastic olefin elastomers), polydimethyl siloxane-based polymers, cross-linked polymers, non-cross linked polymers, Rayon, cellulose, cellulose derivatives such nitrocellulose, natural rubbers, polyesters such as lactides, glycolides, caprolactone polymers and their copolymers, hydroxybutyrate and polyhydroxyvalerate and their copolymers, polyether esters such as polydioxinone, anhydrides such as polymers and copolymers of sebacic acid, hexadecandioic acid and other diacids, orthoesters may be used. Mixtures, copolymers (both block and random) of these materials are also suitable. Polyethylene teraphthalate (PET or Dacron) is a preferred non-biodegradable polymer. In a preferred variation, the polymeric fiber comprises materials which are biodegradable and that have already been approved for use in wound healing in humans. Typically and preferred biodegradable polymers include polyglycolic and polylactic acids.

The pitch of the winding of the polymeric fiber (102, 108) can range from closed to open depending on the desired density of polymer. The resulting primary coil diameter typically is in the range of 0.005 to 0.150 preferably 0.008 and 0.085 inches. Smaller coil diameters are used for finer problems and larger coil diameters and wire diameters are used in larger openings in the human body. A typical coil primary diameter is 0.007 and 0.018 inches. The axial length of a vaso-occlusive device may be between 0.5 and 100 centimeters. The coils are typically wound to have between 10 and 75 turns per centimeter.

In the variation detailed in FIG. 1A, at least one polymeric fiber (102) is first wound over a wire (104). While this variation discusses winding the fiber (102) over the wire (104), the invention includes the act of braiding the fiber (102) about the wire (104) as well. The polymer tends to flatten onto the wire, taking on a low profile and the appearance of a ribbon. The covered wire is then formed into a primary shape, for example a coil, by winding the primary shape about a cylindrical or conical mandrel. Other suitable primary shapes include braids, ribbons or the like. Preferably, the primary shape is formed by using a closed pitch winding over a mandrel diameter of between about 0.005 and about 0.009 inches. Larger or smaller mandrels and open pitches may also be employed. The occlusion devices of the invention may be made using conventional equipment and procedures.

The polymer may be made to adhere to the underlying wire by melting the polymer or by the use of adhesives or by other suitable means. The then-secured polymer covered wire is then rolled into a helical shape.

FIG. 1B depicts a typical vaso-occlusive device (100) in which a wire (104) has been formed into the primary shape of a helical coil. The helical coil is then covered with a wrapped polymeric fiber (108) using the procedures described below. Vaso-occlusive device (100), as shown in FIG. 1B, comprises a helically wound coil having tips (106) to ease the potential of the component wire to cause trauma in a blood vessel. The device comprises a wire (104) wrapped in a closed pitch fashion with a polymeric fiber (108). Heat may be applied to the wrapped polymeric fiber prior to the placement of the fiber (108) on the wire (104) or subsequent to the placement of the fiber on the coiled wire (104) to provide some form to the polymeric fiber.

Figure 1C:
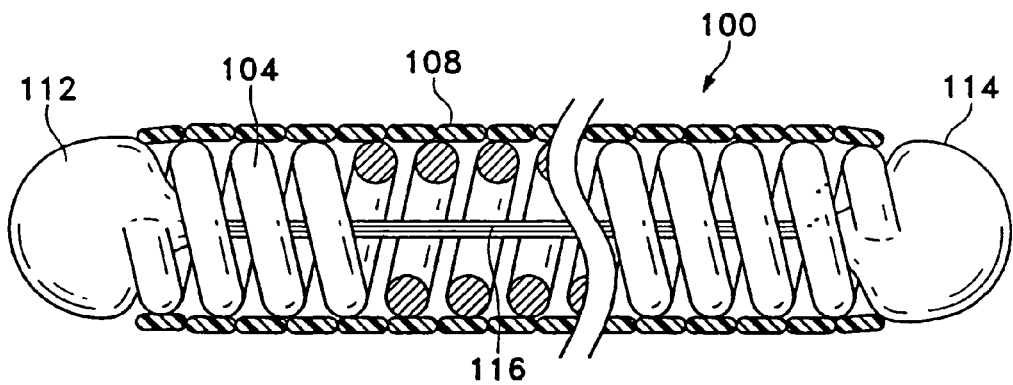
FIG. 1C shows a side view, partial cutaway of a vaso-occlusive coil made according to the invention having a generally linear fibrous stretch-resisting member.
Figure 1D:
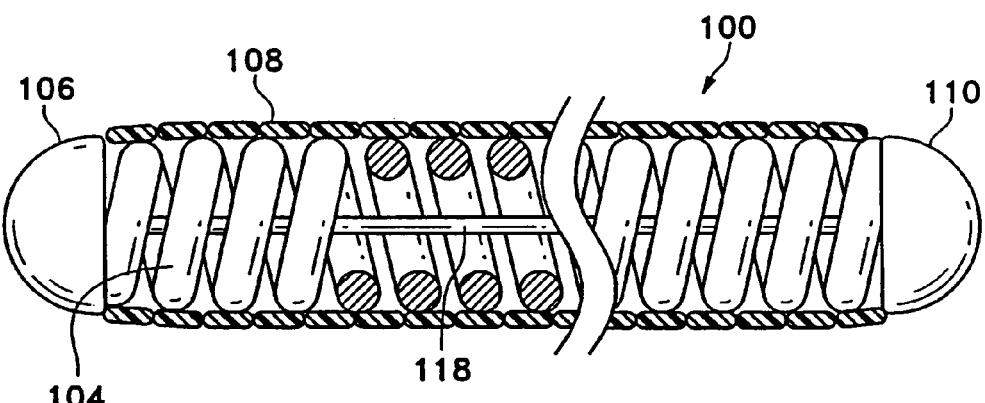
FIG. 1D shows a side view, partial cutaway of a vaso-occlusive coil made according to the invention having a generally linear wire stretch-resisting member.
Figure 1E:
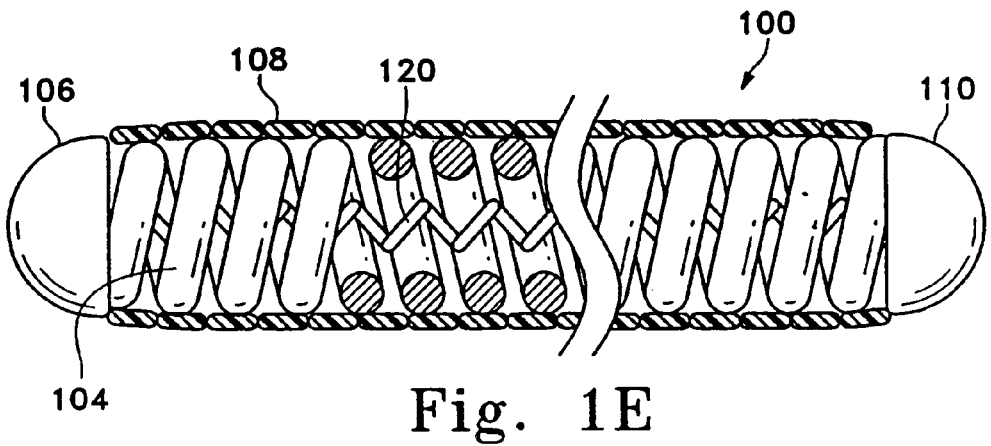
FIG. 1E shows a side view, partial cutaway of a vaso-occlusive coil made according to the invention having a generally helical stretch-resisting member.

FIGS. 1C, 1D, and 1E show side-view partial cross-sections of variations of the inventive coil with stretch-resistant members. In these illustrations, the polymeric covering (108) is shown to be wrapped about the primary shape (104) for illustrative purposes only. The use of a wire wrapped with at least one polymeric fiber (not shown) is also contemplated with these variations of the inventive device.

The variations shown in FIGS. 1C and 1D are made up of a helically wound outer coil (104) having a first end (106, 112) and a second end (110, 114). These variations include a stretch-resisting member (116,118) which is shown to be fixedly attached both to the first end (106, 112) and to the second end (110, 114). In certain circumstances, it may be desirable to attach the stretch-resisting member (116, 118) only to one of the two ends, to at least one site between the to ends, or to neither of the two ends. Clearly, for attaining stretch resistance, the stretch-resisting member must be attached to at least two points on the coil.

The stretch-resisting member (116) of the variation shown in FIG. 1C is fibrous and desirably polymeric. The stretch-resisting member (116) may be thermoplastic or thermosetting and comprise a bundle of strands or a single strand melted onto, glued, or otherwise fixedly attached to the vaso-occlusive coil (100).

In this variation of the invention, the stretch-resisting member is preferably a polymer (natural or synthetic) which may be heat-set in the secondary form in situ. The use of heat-treated or heat-formed polymeric strand (single or multiple) should not affect the secondary shape of the coil and provides stretch resistance while allowing the selected form of the device to perform its occlusive function without interference from the safety component. In some instances, it may also be desirable to include one or more metallic strands in the stretch-resisting member (116) to provide stiffness or electrical conductance for specific applications.

The stretch-resisting member (118) of the variation shown in FIG. 1D is a simple wire or "ribbon" which is soldered, brazed, glued, or otherwise fixedly attached to the first end (106), second end (110), or to the coil at one or more locations intermediate to those the ends.

The variation shown in FIG. 1E includes a stretch-resisting member (120) which is comprised of a helically wound coil which is soldered, brazed, glued, or otherwise fixedly attached to the first end (106) or second end (110) or in one or more intermediate locations. The stretch-resisting member (120) in this configuration provides a greater measure of lateral flexibility than the wire variation (118 in FIG. 1D). It may be wound in either the same direction as is the outer coil (104) or in the alternate direction. A modest drawback to this variation is that it will stretch more than the FIG. 1D variation when axially stressed.

The materials used in constructing the stretch-resisting member (116, 118, 120) may be any of a wide variety of materials; preferably, a radio-opaque material such as a metal or a polymer is used. Suitable metals and alloys the stretch-resisting member (116, 118, 120) include the Platinum Group metals, especially platinum, rhodium, palladium, rhenium, as well as tungsten, gold, silver, tantalum, and alloys of these metals. These metals have significant radio-opacity and in their alloys may be tailored to accomplish an appropriate blend of flexibility and stiffness. They are also largely biologically inert. Highly preferred is a platinum/tungsten alloy, e.g., 8% tungsten and the remainder platinum.

In some variations of the invention, the ribbon or coil stretch-resisting members (116, 118, 120) may be of any of a wide variety of stainless steels if some sacrifice of radio-opacity and flexibility may be tolerated. Very desirable materials of construction, from a mechanical point of view, are materials which maintain their shape despite being subjected to high stress. Certain "super-elastic alloys" include various nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is the titanium/nickel alloy known as "nitinol". These are very sturdy alloys which will tolerate significant flexing without deformation even when used as very small diameter wire.

If a super-elastic alloy such as nitinol is used in the device, the diameter of the coil wire may be significantly smaller than that used when the relatively more ductile platinum or platinum/tungsten alloy is used as the material of construction.

Once the primary coil (104) is wound, the stretch-resisting member (116, 118, 120) is inserted into the lumen of the primary coil (104) and secured to the coil as desired. Ends (106, 112, 110, 114) are preferably of the same diameter as is the primary coil (104).

Alternatively, the primary coil is shaped into its secondary form, and heat treated so that the coil will return to the secondary form when relaxed. The stretch-resistant member is then inserted into the lumen of the coil and secured as desired. The stretch-resisting member does not substantially affect the shape of the coil when the coil returns to the secondary form. Preferably, the stretch-resistant member is attached to a hook inside the lumen and heat treatment used to fuse at least parts of the polymer to the coil. The coil is then allowed to relax to form its secondary form and any stretch-resistant filaments extending from the coil are heat sealed to the coil. It is required that there be some amount of slack in the polymer to allow the coil to pass through the catheter as described herein and to allow the coil to return to its secondary form. The secondary coil may be heated treated. Preferably, heat treatment occurs at a temperature from at least about the $T_g$ of the polymer to a temperature below the melting point of polymer.

Suitable polymeric materials for the polymeric stretch-resisting member (116, 118, 120) can be either thermosetting or thermoplastic. For this variation of the invention, however, the polymer should be one for which a strand may be heat-treated to accept a form corresponding to the secondary form. Thermoplastics are preferred because they allow simplification of the procedure for constructing the device (100) since they may be melted and formed into the end or ends (106, 112, 110, 114). Simple devices such as soldering irons may be used to form the ends. Thermosetting plastics would typically be held in place by an adhesive. Suitable polymers include most biocompatible materials which may be made into fibers but include thermoplastics, e.g., polyesters such as polyethyleneterephthalate (PET) especially Dacron; polyamides including the Nylons; polyolefins such as polyethylene, polypropylene, polybutylene, their mixtures, alloys, block and random copolymers; polyglycolic acid; polylactic acid; fluoropolymers (polytetrafluoro-ethylene), or even silk or collagen. The stretch-resistant polymer may be made from materials used as dissolvable sutures, for instance polylactic acid or polyglycolic acid, to encourage cell growth in the aneurysm after their introduction. Preferred because of the long history of safe and effective usage in the human body are fibrous PET (sold as Dacron) and polypropylene. Highly preferred is polypropylene, for instance, in the form of 10-0 and 9-0 polypropylene suture material. We have found that the diameter of the polymer is typically between about 0.0001 inches and about 0.01 inches.

Figure 1F:
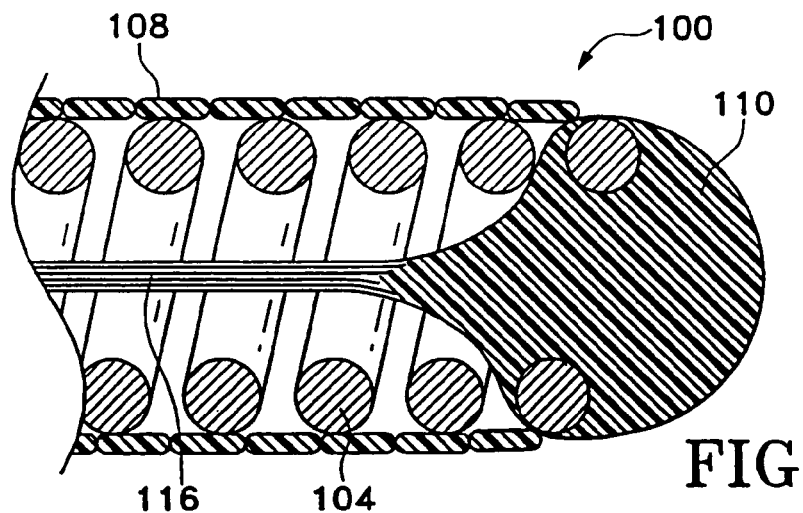
FIGS. 1F, 1G, and 1H show side view, partial cutaways of typical ends of the inventive vaso-occlusive coils.
Figure 1G:
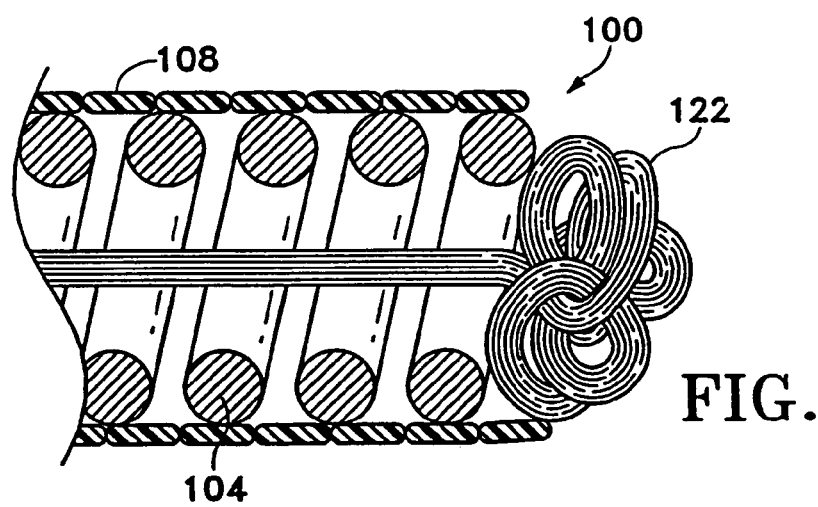
Figure 1H:
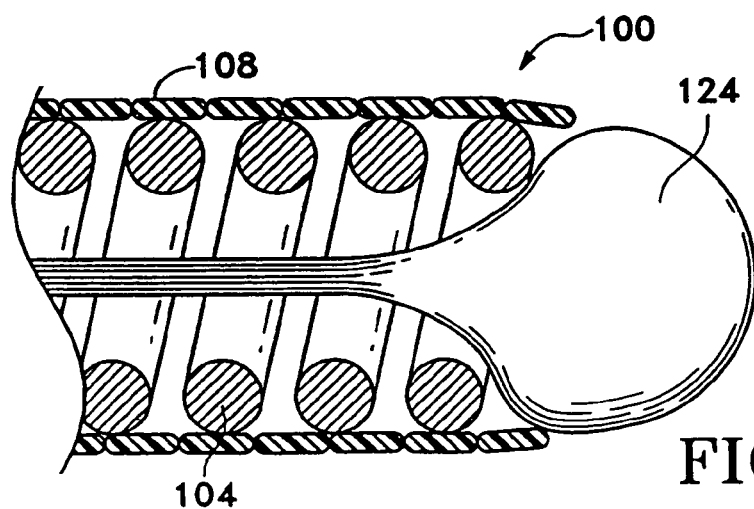

FIGS. 1F, 1G, and 1H show side-view partial cross-sections of an end of inventive coil (100). Again, in these illustrations, the polymeric covering (108) is shown to be wrapped about the primary shape (104) for illustrative purposes only. The use of a wire wrapped with at least one polymeric fiber (not shown) is also contemplated with these variations of the inventive device. FIG. 1F also shows the helically wound outer coil (104) having an end (110) which is formed from a formerly molten strand which also makes up the stretch-resisting member (116). An end of this type may be considered to have modestly higher vaso-occluding properties than a metallic end. Other functional equivalents to this structure include ends (110) formed of glues such as epoxies and their equivalents, and which are mechanical in nature.

FIG. 1G shows an external knot (122) which fixes the length of the coil member (104) and keeps it from stretching; FIG. 1H shows a reformed mass of formerly molten polymer or of glue which is of a diameter larger than the inner diameter of coil (104) and prevents the coil from stretching. The knot (122) and block (124) are not shown to be attached to the coil (104) but may be.

The vaso-occlusive devices shown are illustrative of the coils described below.

FIG. 2A-2G illustrates a vaso-occlusive device (100) of this invention having a secondary shape. These shapes are simply indicative of the various secondary shapes suitable for this invention. Other shapes may be used as well. While not shown, the devices illustrated in FIGS. 2A-2G incorporate the polymeric fiber as provided in FIGS. 1A-1B. The device (100) may be, but is not necessarily, subjected to a heating step as known to one skilled in the art to set the device into a secondary shape. As previously mentioned, the devices (100) having secondary shapes, may, but are not limited to including a stretch resisting member.

Figure 2A:
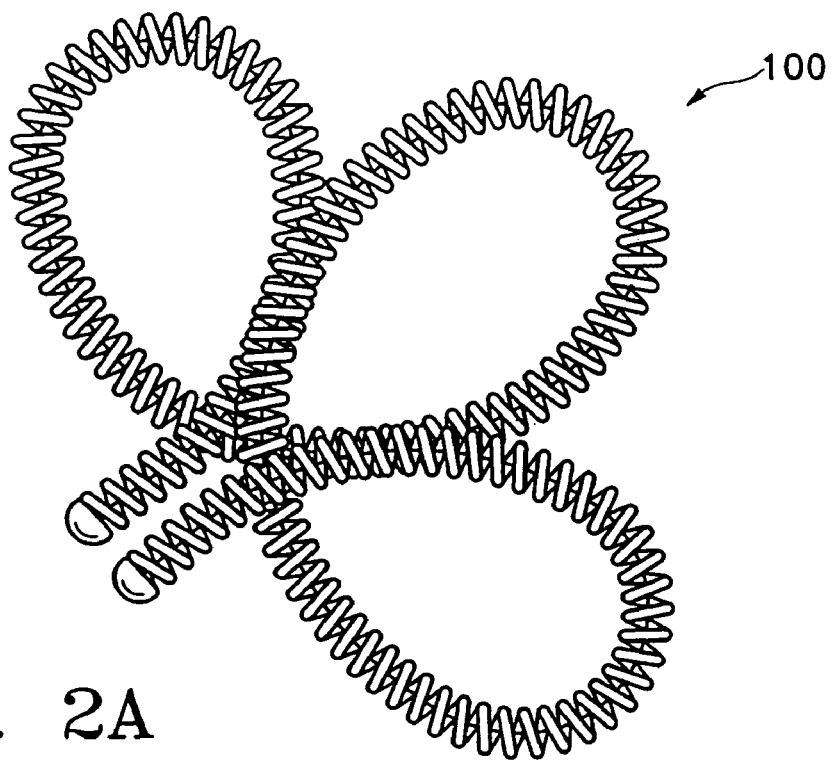
FIGS. 2A-2G illustrate variations of a polymeric covered occlusion device having secondary shapes.
Figure 2B:
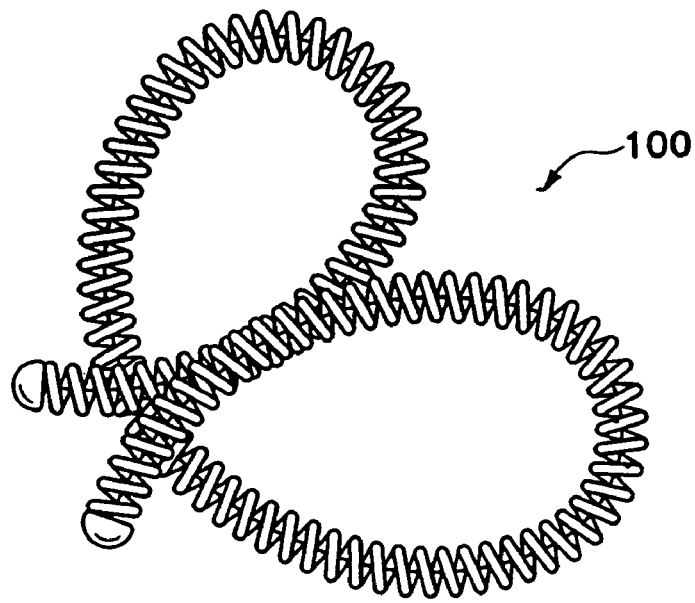
Figure 2C:
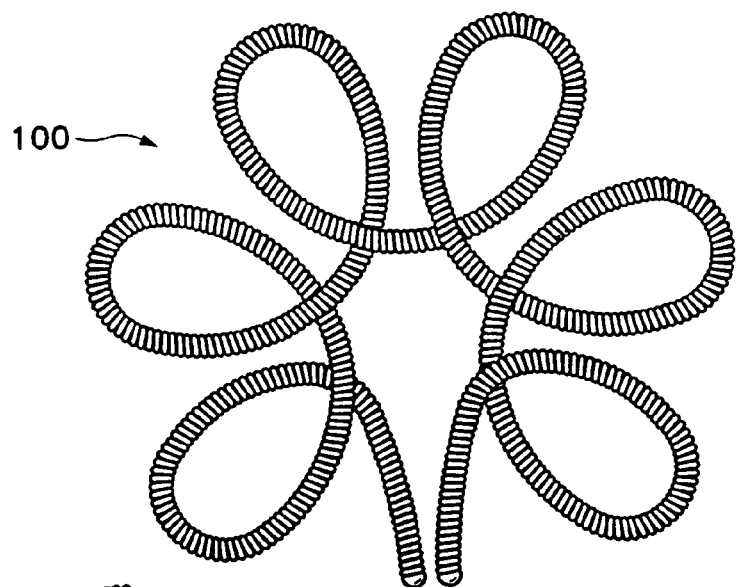
Figure 2D:
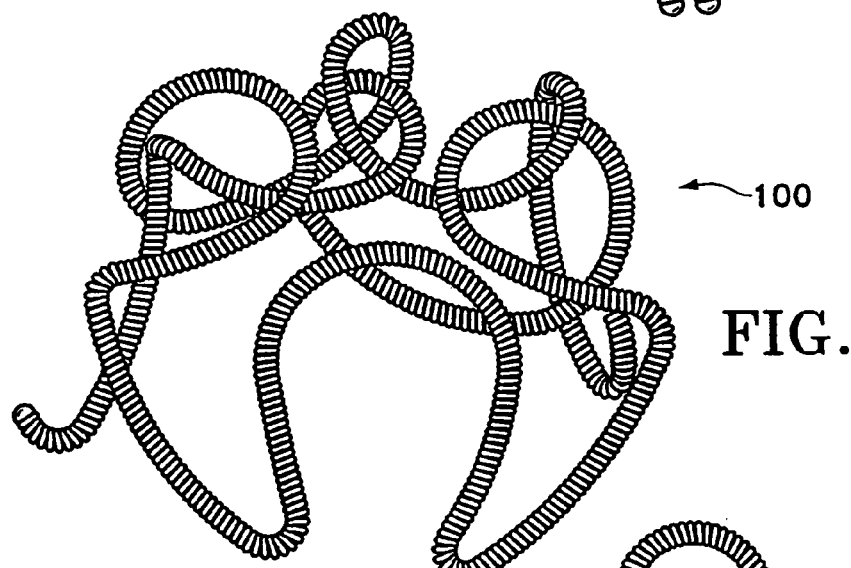
Figure 2E:
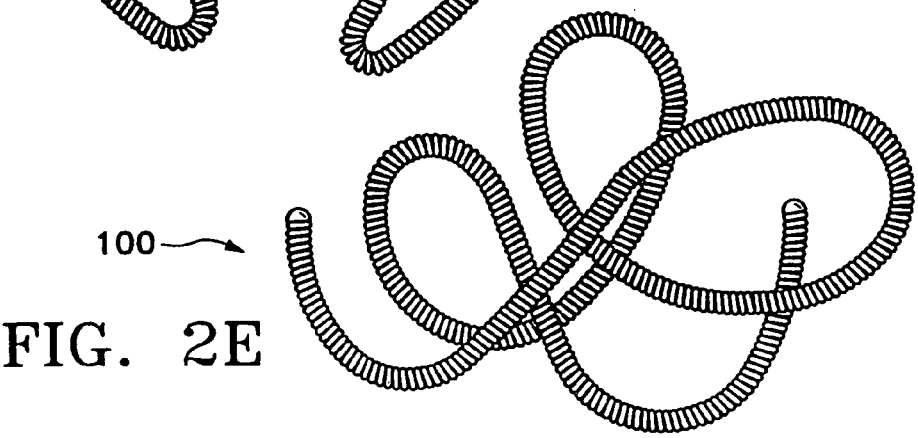
Figure 2F:
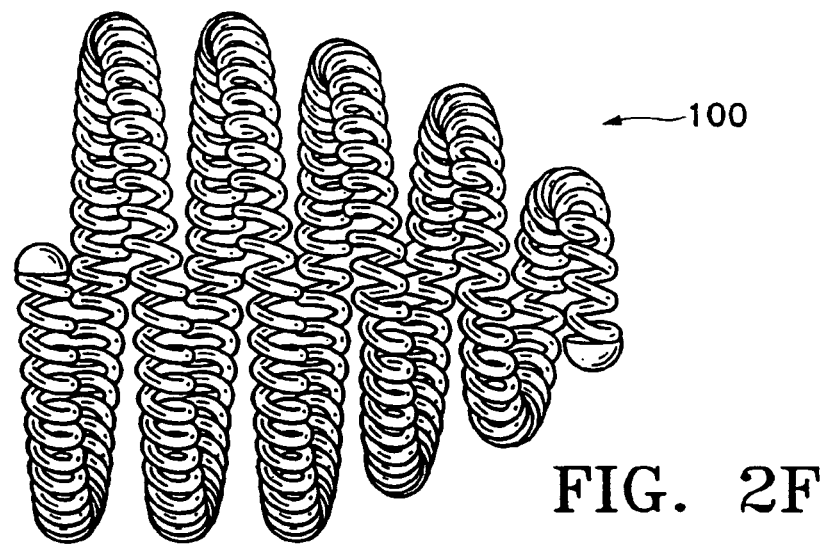
Figure 2G:
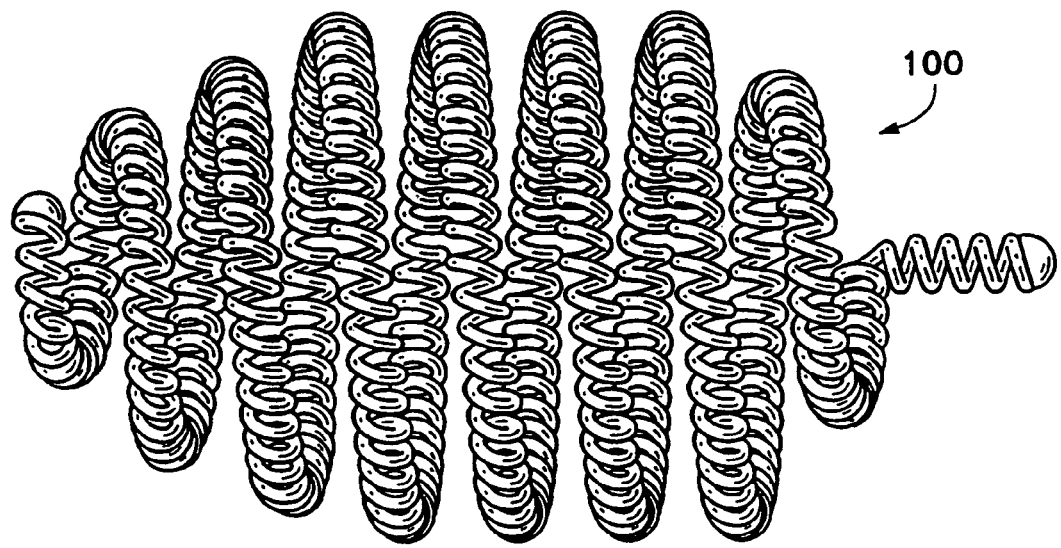

FIG. 2A depicts a device (100) having a secondary shape of a clover leaf FIG. 2B depicts a device (100) having a secondary shape of a twisted figure 8. FIG. 2C depicts a device (100) having a flower-shaped secondary shape. FIG. 2D depicts a device (100) having a substantially spherical secondary shape. FIG. 2E illustrates a device (100) having a random secondary shape. FIG. 2F illustrates a device (100) having secondary shape of a vortex. FIG. 2G illustrates a device (100) having a secondary shape of an ovoid.

Figure 3:
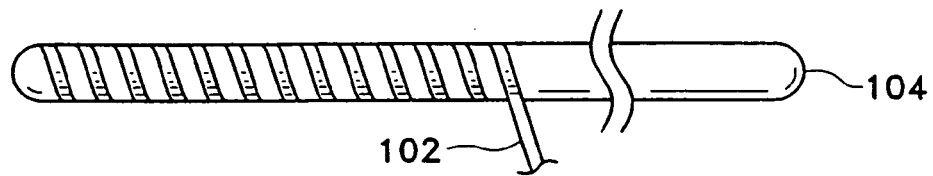
FIG. 3 illustrates the method of winding or braiding at least one polymeric fiber about a wire.

FIG. 3 illustrates, the method of wrapping at least one polymeric fiber (102) about a wire (104) which is subsequently formed into a primary shape (not shown.) The wire (104) is rotated and the polymeric fiber (102) is simply wound onto the rotating wire. As mentioned above, the pitch of the fiber (102) may be either open or closed. The polymeric fiber (102) may be made to adhere to the wire (104) at one or more places. The fiber (102) itself may be sticky by, e.g., addition of such adhesives as ethylvinylacetate (EVA) to the polymer or onto the fiber itself.

Figure 4:
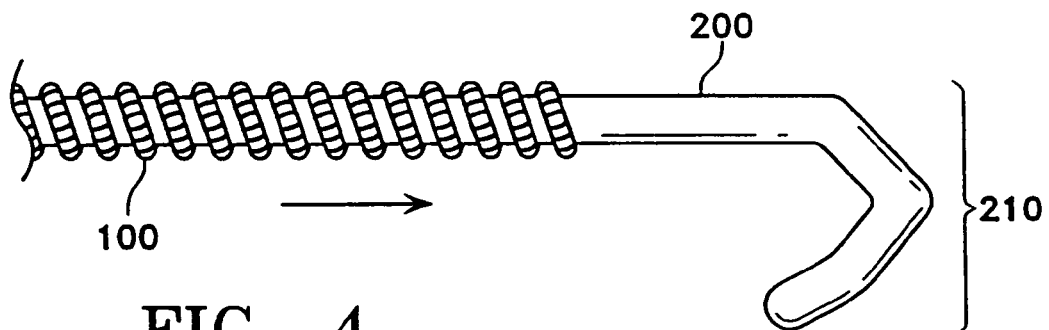
FIG. 4 illustrates a method of shaping a secondary shape by pulling a stylet through a primary shape of a polymeric wrapped wire.

FIG. 4 depicts a method of forming a secondary shape from the primary polymer covered shape. A stylet, mandrel, or shaping element (200) having a specific tip shape (210) is pulled through the inner diameter of the device (100), thereby mechanically working and shaping the device (100). In some instances, the mandrel may be used along with heat to shape the device.

Not shown is the step of further heating a polymeric covered device after the device is formed into a secondary shape. This additional heating step may be used to set the polymeric material to the secondary shape of device (100).

Figure 5A:
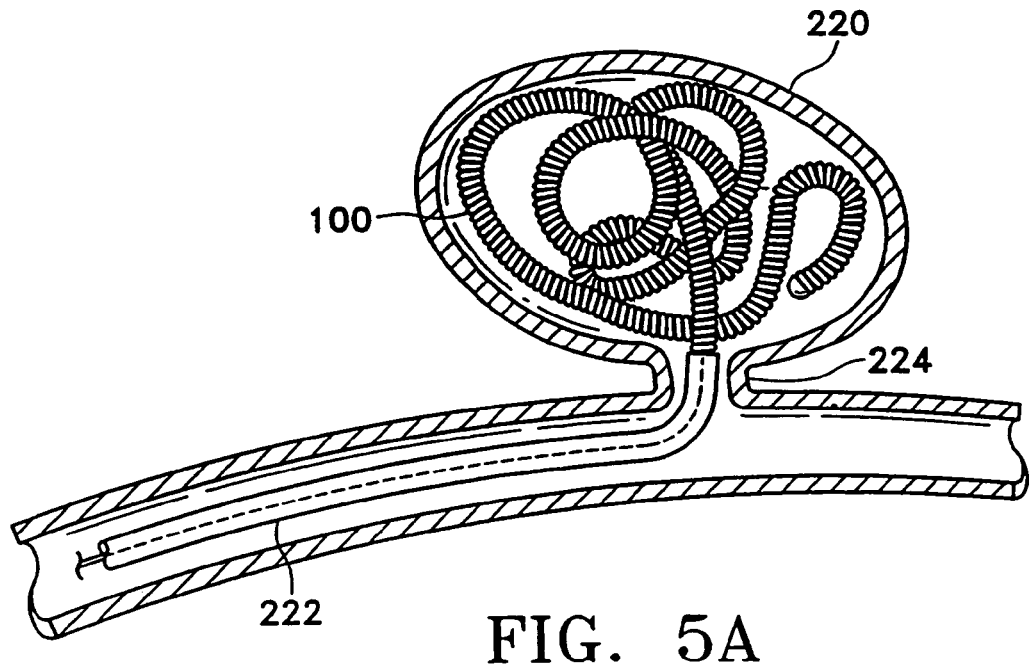
FIG. 5A illustrates a method of deploying a polymeric covered occlusion device to at least partially occlude an aneurysm.

FIG. 5A illustrates the deployment of the device (100) into an aneurysm (220). In this instance, the device (100) is placed in the aneurysm (220) with the aid of a catheter (222). The catheter (222) is maneuvered to the neck (224) of the aneurysm (220). In this example, the device (100) has a random secondary shape, however, the device (100) may have any shape as the situation requires.

Figure 5B:
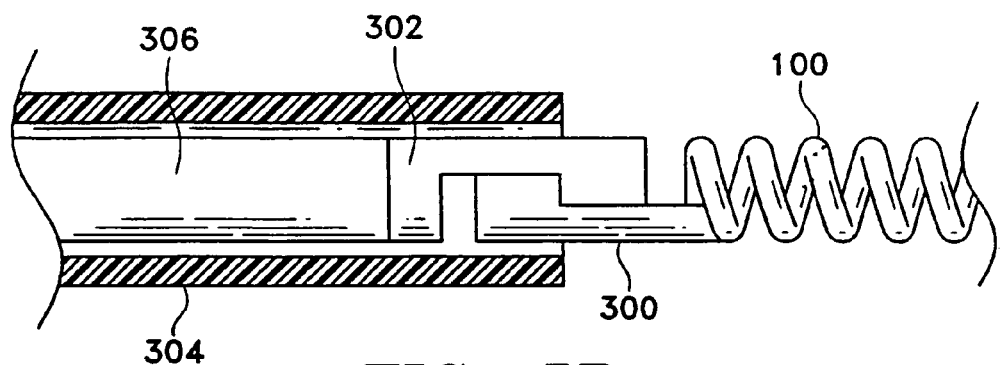
FIG. 5B illustrates a polymeric covered occlusion device with an mechanically detachable tip.

FIG. 5B illustrates a variation of a device (100) having a mechanically detachable tip (300). The device is deployed using a delivery device (304) e.g., a catheter, and a pusher (306) having a mechanically detachable tip (302). When the delivery device (304) is withdrawn, the more proximal mechanically detachable tip (302) is able to separate from the mechanically detachable tip (300) lodged on the coil (100).

Figure 5C:
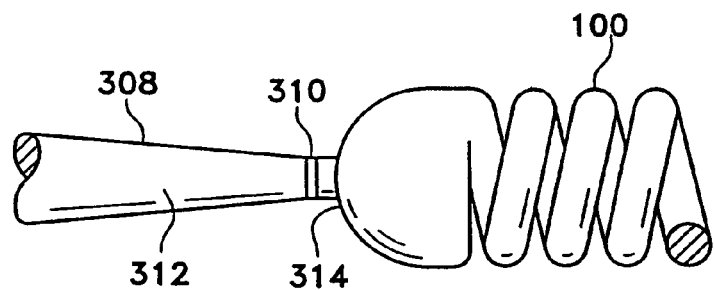
FIG. 5C illustrates a polymeric covered occlusion device with a electrolytically detachable tip.

FIG. 5C illustrates a variation of a device (100) having an electrolytically detachable tip (314). The device (100) is delivered via a pusher (308) having an electrolytically detachable tip (312). The device (100) is connected to the pusher (308) via an electrolytically detachable joint (310). When the device (100) is placed as desired in the aneurysm (220), the electrolytically detachable joint (310) is dissolved via applying an appropriate electrical current to the pusher (308). The Guglielmi patent described above provides an expanded explanation of how the electrolytically severable joint operates.

Figure 5D:
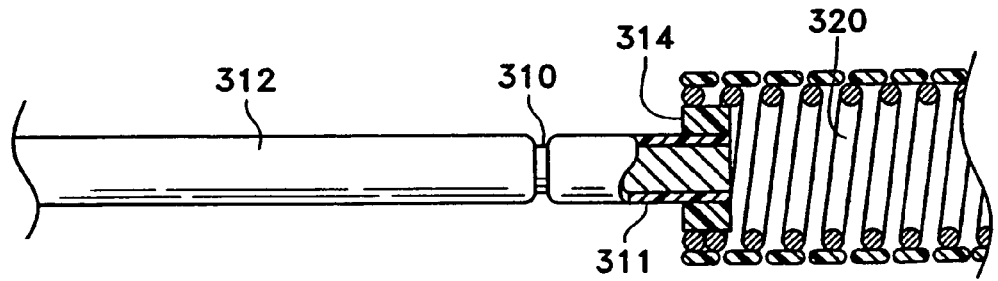
FIG. 5D illustrates a polymeric covered occlusion device with a electrolytically detachable tip with a highly resistive or insulative member proximally of the implant.

FIG. 5D illustrates a variation of the electrolytic joint with an insulative layer. FIG. 5D shows a close-up of the more distal portion of one variation of the invention. This variation includes the core wire (310) and the attached implant (320). Typically, core wire (310) will be conductive but covered with a insulative layer (311) both proximal and distal of electrolytically severable joint (312). The interior of core wire (310) is physically attached to implant (320). In this variation of the invention, implant (320) is a helically wound coil.

In this variation, a highly resistive or insulative layer or member electrically isolates implant (320) from core wire (310). In this variation of the invention, the insulating layer (311) on the core wire (310) is simply continued to the end of the core wire (310). An optional bushing (314) is placed on the core wire (310) to further separate it from implant (320). Optional bushing (314) may be of any suitable material since it operates merely as a spacer. Insulating layer (311) may be polytetrafluoroethylene (e.g., Teflon), polyparaxylxylene (e.g., Parylene), polyethyleneterephthalate (PET), polybutyleneterephthalate (PBT), cyanoacrylate adhesives, or other suitable insulating layer, but preferably is polymeric and most preferably is PET.

The devices made according to the procedure of this invention may be introduced to a selected site within the body using the procedure such as the one outlined below. This procedure may be used in treating a variety of maladies. For instance, in treatment of an aneurysm (220), the aneurysm (220) itself may be filled with the devices made according to the procedure specified here. Shortly after the devices are placed within the aneurysm (220), it is thought that the outer coating causes an irritation at the site. An emboli begins to form and, at some later time, is at least partially replaced by highly vascularized material which is at least partially collagenous. This mass is formed around the inventive vaso-occlusive devices.

In general, a selected site is reached through the vascular system using a collection of specifically chosen catheters and guide wires. It is clear that should the aneurysm (220) be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson.

First of all, a so-called "introducer" catheter is introduced through an entry site in the vasculature. Typically, this would be through a femoral artery in the groin. Other entry sites sometimes chosen are found in the neck and are in general well known by physicians who practice this type of medicine. Once the introducer is in place, a smaller but still fairly large catheter, such as a guiding catheter, is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. The guide catheter would terminate in the region just above the neck. A guidewire and neurovascular catheter such as that described in the Engelson patent are then placed through the guiding catheter as a unit. Once the tip of the guidewire reaches the end of the guiding catheter, it is then extended using fluoroscopy, by the physician to the site to be treated. During the trip between the treatment site and the guide catheter tip, the guidewire is advanced for a distance and the neurovascular catheter follows. Once both the distal tip of the neurovascular catheter and the guidewire have reached the treatment site, and the distal tip of that catheter is appropriately situated, e.g., within the mouth of an aneurysm (220) to be treated, the guidewire is then withdrawn. The neurovascular catheter then has an open lumen to the outside of the body. The devices of this invention are then pushed through the lumen to the treatment site. They are held in place variously because of their shape, size, or volume. These concepts are described in the Ritchart et al patent as well as others. Once the vaso-occlusive devices are situated in the vascular site, the embolism forms.

In another variation, the polymeric fiber covering the device are used as a carrier for bioactive molecules. Non-limiting examples of bioactive materials which increase cell attachment and/or thrombogenicity include both natural and synthetic compounds, e.g., collagen, fibrinogen, vitronectin, other plasma proteins, growth factors (e.g., vascular endothelial growth factor, "vEGF"), synthetic peptides of these and other proteins having attached RGD (arginine-glycine-aspartic acid) residues, generally at one or both termini. In addition, polynucleotide sequences encoding peptides (e.g., genes) involved in wound healing or promoting cellular attachment may also be used.

Modifications of the procedure and device described above, and the methods of using them in keeping with this invention will be apparent to those having skill in this mechanical and surgical art. These variations are intended to be within the scope of the claims that follow.

The invention claimed is:

1. A vaso-occlusive device, comprising:
a solid wire configured to occlude a vascular site, the solid wire formed into a primary shape, the solid wire being helically wrapped with one of a polyether fiber material and acrylate fiber material in a non-braided, non-woven configuration; wherein the one of a polyether fiber material and acrylate fiber material is wrapped in a helix around the longitudinal axis of the solid wire.

2. The vaso-occlusive device of claim 1, wherein the polyether fiber material is wound about the solid wire with a closed pitch.

3. The vaso-occlusive device of claim 1, wherein the polyether fiber material is wound about the solid wire with an open pitch.

4. The vaso-occlusive device of claim 1, wherein the polyether fiber material comprises a radiopaque additive.

5. The vaso-occlusive device of claim 1, wherein the solid wire is radiopaque.

6. The vaso-occlusive device of claim 1, further comprising a detachable tip.

7. The vaso-occlusive device of claim 6, the detachable tip comprising an electrolytically severable joint attached to the solid wire, the electrolytically severable joint being more susceptible to electrolysis in an ionic solution than the solid wire, wherein the device is electrically isolated from the electrolytically severable joint.

8. The vaso-occlusive device of claim 1, the primary shape comprising a substantially helical coil.

9. The vaso-occlusive device of claim 8, the solid wire having a secondary shape.

10. The vaso-occlusive device of claim 9, wherein the secondary shape is selected from the group consisting of clover-leaf shaped, figure-8 shaped, flower-shaped, vortex-shaped, ovoid, randomly shaped, and substantially spherical.

11. The vaso-occlusive device of claim 9, further comprising a stretch-resisting member having a first end and a second end, the stretch-resisting member being attached to the device in at least two locations and extending through at least a portion of an interior of the primary shape, the stretch-resisting member not substantially affecting the secondary shape.

12. The vaso-occlusive device of claim 1, the polyether fiber material comprising a mono-filament.

13. The vaso-occlusive device of claim 1, the polyether fiber material comprising a plurality of filaments.

14. The vaso-occlusive device of claim 1, the polyether fiber material being a cross linked polyether material.

15. The vaso-occlusive device of claim 1, wherein the acrylate fiber material is wound about the wire with a closed pitch.

16. The vaso-occlusive device of claim 1, wherein the acrylate fiber material is wound about the wire with an open pitch.

17. The vaso-occlusive device of claim 1, wherein the acrylate fiber material comprises a radiopaque additive.

18. The vaso-occlusive device of claim 1, wherein the acrylate fiber material comprises a mono-filament.

19. The vaso-occlusive device of claim 1, wherein the acrylate fiber material comprises a plurality of filaments.

20. The vaso-occlusive device of claim 1, wherein the acrylate fiber material is a cross linked acrylate material.

21. The vaso-occlusive device of claim 1, wherein the fiber material is absorbable.

22. A vaso-occlusive device, comprising:
   a solid wire configured to occlude a vascular site, the solid wire formed into a primary shape, wherein a polyether fiber material is wound about the solid wire formed in the primary shape in a helical, non-braided, non-woven configuration, wherein the polyether fiber material is wound in a helix around a longitudinal axis of the primary shape.

* * * * *

UNITED STATES PATENT AND TRADEMARK OFFICE
CERTIFICATE OF CORRECTION

PATENT NO.        : 7,695,484 B2                                        Page 1 of 1
APPLICATION NO. : 11/089829
DATED             : April 13, 2010
INVENTOR(S)       : Wallace et al.

It is certified that error appears in the above-identified patent and that said Letters Patent is hereby corrected as shown below:

On the Cover Page:

At item (75) Inventors, the correct spelling of second inventor shown as follows:

Delete "Dewlilah" and insert therefore --Delilah--

Signed and Sealed this

Fifteenth Day of June, 2010

David J. Kappos
*Director of the United States Patent and Trademark Office*